(12) United States Patent
Chlon et al.

(10) Patent No.: US 10,456,199 B2
(45) Date of Patent: Oct. 29, 2019

(54) DEVICE FOR FRACTIONAL LASER-BASED-TREATMENT

(71) Applicant: KONINKLIJKE PHILIPS N.V., Eindhoven (NL)

(72) Inventors: Caecilia Hendrina Theodora Chlon, Eindhoven (NL); Martin Jurna, Eindhoven (NL); Antonius Maarten Nuijs, Eindhoven (NL); Maria Angelina Josepha Grootel-Rensen, Eindhoven (NL); Bastiaan Wilhelmus Maria Moeskops, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 724 days.

(21) Appl. No.: 14/907,869

(22) PCT Filed: Jul. 30, 2014

(86) PCT No.: PCT/EP2014/066325
§ 371 (c)(1),
(2) Date: Jan. 27, 2016

(87) PCT Pub. No.: WO2015/014868
PCT Pub. Date: Feb. 5, 2015

(65) Prior Publication Data
US 2016/0175049 A1    Jun. 23, 2016

(30) Foreign Application Priority Data

Jul. 30, 2013   (EP) .................................... 13178527

(51) Int. Cl.
*A61B 5/06*   (2006.01)
*A61B 18/20*  (2006.01)
(Continued)

(52) U.S. Cl.
CPC .. *A61B 18/203* (2013.01); *A61B 2017/00075* (2013.01); *A61B 2018/0047* (2013.01);
(Continued)

(58) Field of Classification Search
CPC ........ A61B 18/203; A61B 2018/20351; A61B 2017/00075; A61B 2018/00452;
(Continued)

(56) References Cited

U.S. PATENT DOCUMENTS

| 8,353,899 B1 | 1/2013 | Wells |
| 2005/0143719 A1* | 6/2005 | Sink ..................... A61B 18/203 606/9 |

(Continued)

FOREIGN PATENT DOCUMENTS

| GB | 2486919 A | 7/2012 |
| WO | 02094116 A1 | 11/2002 |
| WO | 2008002625 A2 | 1/2008 |
| WO | 2013036761 A1 | 3/2013 |

*Primary Examiner* — Aaron F Roane

(57) ABSTRACT

A treatment device for fractional laser-based skin treatment includes an emission window having an elongated area and predefined locations that are arranged in an elongated array which extends along a treatment axis of the window. A treatment generator has a treatment laser for emitting laser light towards skin tissue from the predefined locations in the emission window for generating, in use, laser-based lesions inside the skin tissue. The treatment device also includes a motion sensor for sensing motion of the treatment device relative to the skin surface, and a controller for determining a non-zero sequence of at least one of the predefined locations from which laser light is consecutively emitted in dependence on the sensed motion. The controller allows generation of the non-zero sequence when the sensed motion of the treatment device relative to the skin surface only has a component in a direction parallel to the treatment axis.

16 Claims, 7 Drawing Sheets

(51) Int. Cl.
*A61B 18/00* (2006.01)
*A61B 17/00* (2006.01)

(52) U.S. Cl.
CPC ............... *A61B 2018/00452* (2013.01); *A61B 2018/00636* (2013.01); *A61B 2018/00642* (2013.01); *A61B 2018/00672* (2013.01); *A61B 2018/00684* (2013.01); *A61B 2018/00702* (2013.01); *A61B 2018/208* (2013.01); *A61B 2018/20351* (2017.05); *A61B 2018/20359* (2017.05); *A61B 2018/205547* (2017.05)

(58) Field of Classification Search
CPC .. A61B 2018/0047; A61B 2018/00636; A61B 2018/00642; A61B 2018/00672; A61B 2018/00684; A61B 2018/00702; A61B 2018/202; A61B 2018/208
USPC ............................................................ 606/9
See application file for complete search history.

(56) References Cited

U.S. PATENT DOCUMENTS

| | | |
|---|---|---|
| 2007/0265604 A1 | 11/2007 | Davenport |
| 2009/0069741 A1* | 3/2009 | Altshuler ............... A61B 5/441 604/22 |
| 2010/0241109 A1 | 9/2010 | Floessholzer |
| 2012/0197357 A1 | 8/2012 | Dewey |
| 2012/0283709 A1 | 11/2012 | Reichert |
| 2012/0283712 A1 | 11/2012 | Youngquist |

* cited by examiner

| hand speed [cm/s] | Area 'coverage' [lesions/cm2] | fire frequency (Hz) | laser duty cycle [%] |
|---|---|---|---|
| 0,5 | 30 | 15 | 4,2 |
| 1,0 | 30 | 30 | 8,3 |
| 1,5 | 30 | 45 | 12,5 |
| 2,0 | 30 | 60 | 16,7 |
| 2,5 | 30 | 75 | 20,8 |
| 3,0 | 30 | 90 | 25,0 |
| 3,5 | 30 | 105 | 29,2 |
| 4,0 | 30 | 120 | 33,3 |
| 4,5 | 30 | 135 | 37,5 |
| 5,0 | 30 | 150 | 41,7 |
| 5,5 | 30 | 165 | 45,8 |
| 6,0 | 30 | 180 | 50,0 |

Fig. 5A

| laser duty cycle [%] | Fire Frequency [Hz] | Facet location | | | | | | | |
|---|---|---|---|---|---|---|---|---|---|
| | | 1 | 2 | 3 | 4 | 5 | 6 | 7 | 8 |
| 50 | 180 | x | x | x | x | x | x | x | x |
| 44 | 157 | x | x | x | | x | x | x | x |
| 38 | 135 | x | x | | x | x | | x | x |
| 31 | 112 | x | x | x | | x | | x | |
| 25 | 90 | | x | | x | | x | | x |
| 19 | 67 | x | | | x | | | x | |
| 13 | 45 | | x | | | x | | | |
| 6 | 22 | | | | x | | | | |

Fig. 5B

| Vh = hand speed [cm/s] | Angle (90-α) [degrees] | x [cm/s] | y [cm/s] | Line 'coverage' [lesions/cm] | laser duty cycle [%] | Fire Frequency [Hz] |
|---|---|---|---|---|---|---|
| 1,0 | 90 | 0,00 | 1,0 | 10 | 2,8 | 10 |
| 2,0 | 90 | 0,00 | 2,0 | 10 | 5,6 | 20 |
| 3,0 | 90 | 0,00 | 3,0 | 10 | 8,3 | 30 |
| 4,0 | 90 | 0,00 | 4,0 | 10 | 11,1 | 40 |
| 5,0 | 90 | 0,00 | 5,0 | 10 | 13,9 | 50 |
| 6,0 | 90 | 0,00 | 6,0 | 10 | 16,7 | 60 |

DEVICE FOR FRACTIONAL LASER-BASED-TREATMENT

This application is the U.S. National Phase application under 35 U.S.C. § 371 of International Application No. PCT/EP2014/066325, filed on Jul. 30, 2014, which claims the benefit of International Application No. 13178527.1 filed on Jul. 30, 2013. These applications are hereby incorporated by reference herein.

FIELD OF THE INVENTION

This invention relates to a treatment device for fractional laser-based skin treatment.

BACKGROUND OF THE INVENTION

The desire to maintain a youthful appearance by reducing wrinkles and fine lines in the skin is an important issue in human society. Many techniques have been designed to achieve the above issue, one of which is skin rejuvenation using, for example, fractional photo-thermolysis. This fractional photo-thermolysis may, for example, be used for treatment of fine lines, wrinkles, unevenness of pigmentation and dyschromia. Fractional photo-thermolysis is based on creating micro-zones of damage inside skin tissue within areas or volumes of unaffected skin tissue. The treatment either removes (ablative treatment) or thermally damages skin tissue in the micro-zones. The type of treatment, the density of the micro-zones and the depth of the micro-zones are chosen in relation to the skin treatment required and the type of skin to be treated.

A device for such fractional photo-thermolysis treatment is disclosed in US patent application US 2012/0197357. In this patent application an apparatus, in particular a handheld apparatus, is disclosed for delivering optical energy. The apparatus includes an optical pattern generator inside the housing, which includes a rotatable component configured to continually rotate about a rotation axis in a single direction and to deflect the optical beam during rotation to divide the electromagnetic radiation into pulses that propagate from the housing toward the skin surface and form the fractional pattern at the skin surface. Too high a dose of optical energy locally deposited into the skin tissue is highly undesirable during these treatments, because this may lead to complications and even health risks of the person being treated, as well as to social downtime. Therefore, the known fractional photo-thermolysis treatment device comprises a controller which comprises several safety measures to prevent such damage from occurring. However, these safety measures significantly reduce the freedom to operate the known treatment device, as a result of which the ease of use of the known treatment device is reduced.

Consequently, a drawback of the known fractional photo-thermolysis treatment device is that the safety measures limit the freedom to operate this known treatment device.

US 2012/0283709 discloses a treatment device for fractional laser-based skin treatment, comprising a radiation source, a beam scanning system, and a control system to control the radiation source and the beam scanning system. The control system includes a displacement sensor for determining the displacement of the device relative to the skin and/or a motion/speed sensor for determining the speed, rate or velocity of the device moving or gliding across the skin. The controller is configured to control the beam radiation source and/or the beam scanning system in dependence on the displacement, speed, rate or velocity measured by the displacement sensor or motion/speed sensor.

OBJECT OF THE INVENTION

It is an object of the invention to provide a fractional laser-based skin treatment device which can be operated with an improved degree of freedom.

SUMMARY OF THE INVENTION

A first aspect of the invention provides a treatment device for fractional laser-based skin treatment.

The treatment device according to the first aspect of the invention comprises an emission window comprising an elongated area and a plurality of predefined locations in said elongated area, wherein the predefined locations are arranged in an elongated array which extends along a treatment axis of the window, and wherein each predefined location in the array is located at a distance from the treatment axis, seen in a direction perpendicular to the treatment axis, which is smaller than 25% of a maximum distance between two predefined locations in the array, seen in a direction parallel to the treatment axis. The treatment device further comprises a treatment generator comprising a treatment laser, the treatment generator being configured and arranged for emitting laser light towards skin tissue from said plurality of predefined locations in the emission window for generating, in use, laser-based lesions inside the skin tissue. The treatment device further comprises a motion sensor for sensing motion of the treatment device relative to the skin surface and for generating a motion signal representative of the sensed motion. The treatment device also comprises a controller configured for receiving the motion signal, for determining a non-zero sequence of at least one of the plurality of predefined locations in the emission window from which the laser light is consecutively emitted in dependence on the motion signal, and for activating the treatment generator to generate said non-zero sequence by means of a control signal representative of said non-zero sequence. The controller is configured to activate the treatment generator to generate said non-zero sequence when the sensed motion of the treatment device relative to the skin surface only has a component in a direction parallel to the treatment axis.

As mentioned before, the treatment device for applying fractional laser-based skin treatment typically comprises several safety measures to limit the local deposition of too high a dose of optical energy into the skin tissue. Especially when the treatment device is meant to be sold to, and used by, consumers which are typically non-medical, only marginally trained people, the safety measures for such treatment device are significant. One of the safety measures includes measures to prevent that lesions are disposed too close together or even on top of each other, which may lead to too much damage inside the skin tissue. Especially in the case of treatment devices which are able to treat skin areas, such as the known apparatus for delivering optical energy, the laser light is emitted from a row of predefined locations. With such known apparatus, overlap of lesions may occur when the motion of the treatment device relative to the skin surface is not done correctly by the user. For this reason, the known treatment device has an imposed direction of movement, which is substantially perpendicular to the row of predefined locations. One of the safety measures incorporated in the known treatment device is that the treatment device or the laser is switched off or that the treatment is not started at all when no motion is sensed in a direction perpendicular to the row of predefined locations or perpendicular to the treatment axis. Although this safety measure is important, it also significantly reduces the freedom with which a user can operate the treatment device. The treatment device according to the invention comprises a treatment generator having a treatment laser and being configured for emitting laser light towards the skin tissue from a plurality of predefined locations which cover an elongated area of an emission window. The elongated area extends along the treatment axis and is elongated in a direction parallel to the treatment axis such that a skin area covered by the elongated area will be treated when the treatment device is moved relative to the skin surface. The treatment device comprises the motion sensor for sensing the motion of the treatment device relative to the skin surface and for providing a motion signal to a controller of the treatment device. According to the invention, the controller is configured to activate the treatment generator to generate a non-zero sequence of at least one of the plurality of predefined locations in the emission window when the sensed motion of the treatment device relative to the skin surface only has a component in a direction parallel to the treatment axis. Therefore, switching off of the treatment device is prevented when only a movement parallel to the treatment axis is sensed, which results in improved freedom of use of the treatment device according to the invention.

The controller may also control a distribution of the lesions inside the skin tissue. Thus, in the treatment device according to the invention, the controller may also be configured for adapting the control signal in dependence on the direction of the sensed motion. Therefore, when the movement of the treatment device according to the invention parallel to the treatment axis exceeds a predefined threshold, the controller may, for example, change the control signal provided to the treatment generator to ensure that the disposition of lesions is done differently to ensure a certain density of lesions or even prevent overlap of lesions, while still allowing the treatment process to continue. Such changing of the control signal may include the changing of the sequence of the predefined locations in the emission window from which the laser light is emitted when the device is moved over the skin surface. This change in the sequence may be one way of, for example, maintaining a predefined disposition of lesions or preventing overlap of lesions inside the skin tissue, while the treatment device according to the invention is still being moved in a direction parallel to the treatment axis.

The treatment device according to the invention comprises a plurality of predefined locations covering an elongated area of the emission window. This emission window may, for example, be a window which is moved substantially parallel to the skin surface during treatment. This emission window is of course transparent to the laser light used for generating the lesions inside the skin tissue, and may be composed of glass, plastics or another substance transparent to the wavelength of the laser light used for the treatment. Alternatively, the emission window may be a virtual window and may simply be an opening in the treatment device according to the invention through which the laser light is emitted towards the skin tissue.

In an embodiment of the treatment device, the controller is configured to activate the treatment generator to generate said non-zero sequence when, independent of a direction of the sensed motion relative to the treatment axis, a speed of the sensed motion exceeds a treatment threshold value. Therefore, the treatment device may only start the non-zero sequence of generating lesions inside the skin when a motion is sensed that exceeds the treatment threshold, for example, as a safety measure to prevent overlap of lesions or too small a spacing between lesions during the treatment, independent of the movement direction of the treatment device.

In an embodiment of the treatment device, the controller is configured for controlling the power of the treatment laser in dependence on the motion signal. To achieve laser-based skin treatment, the energy density inside the skin tissue at the micro-zones must be between a minimum value to create a lesion and a maximum value to prevent damage to other parts of the skin tissue. As the treatment device is moved relative to the skin tissue, the power required from the treatment laser to generate an energy density between the minimum and maximum value strongly depends on the speed relative to the skin.

In an embodiment of the treatment device, the predefined locations are disposed on the treatment axis. In this embodiment, the elongated array of predefined locations, from which the laser light is emitted, is a single row of predefined locations on the treatment axis, wherein the distance between each predefined location in the elongated array and the treatment axis, seen in a direction perpendicular to the treatment axis, is zero. If the laser light is pulsed and the treatment device is moved in a direction perpendicular to the treatment axis, such an embodiment would almost automatically prevent the overlap of lesions during the treatment. However, it is also immediately apparent that, when the movement is in a direction parallel to the row of predefined locations, overlap of lesions may occur or the density of the lesions may be too high, especially when the treatment device has a single treatment laser which sequentially selects each of the predefined locations for emitting the laser light to generate the lesions. In such an embodiment, the non-zero sequence may comprise a sequential selection of the predefined locations during the treatment, depending on the sensed motion and the sensed direction of the motion, to ensure that a predefined disposition of lesions is generated, also when the movement of the treatment device has a substantial component in a direction parallel to the row of predefined locations.

It is noted that the invention also covers embodiments wherein the predefined locations in the emission window, from which the laser light is emitted, are not arranged in a single row on the treatment axis. Generally, the invention covers any embodiment wherein the predefined locations are arranged in an elongated array which extends along the treatment axis of the window. Generally the elongated array has an elongated direction of extension which coincides with the direction of the treatment axis. More specifically, the elongated array has a central axis of extension in the elongated direction, which central axis of extension coincides with the treatment axis. More specifically, each predefined location in the array is located at a distance from the treatment axis, seen in a direction perpendicular to the treatment axis, which is smaller than 25% of a maximum distance between two predefined locations in the array, seen in a direction parallel to the treatment axis.

In an embodiment of the treatment device, the sensed motion comprises speed and direction of the treatment device with respect to the treatment axis relative to the skin surface. From the previous discussion it is clear that the direction of the motion is important to determine whether the control signal has to be adapted. Also the speed of the motion is important to ensure that the laser power selected during the treatment is effective in creating lesions but does not cause too much damage to the skin tissue.

In an embodiment of the treatment device, the treatment device is configured to apply an area treatment process wherein, when the treatment device moves in a direction perpendicular to the treatment axis, the treatment device generates an area disposition of lesions inside the skin tissue having a width equal to a length of the elongated area of the emission window, or to apply a line treatment process wherein the treatment device generates a line disposition of lesions inside the skin tissue different from the area disposition, the controller being configured to change from the area treatment process to the line treatment process when a speed component of the sensed motion perpendicular to the treatment line is below a change threshold value. An area treatment process is often used to apply the treatment over a specific area, for example, for treatment of unevenness of the skin tissue, pigmentation or dischroma issues of the skin tissue. For such an area treatment to be time-effective, the treatment device comprises a row or array of predefined locations from which laser light may be emitted from the treatment device to treat multiple locations sequentially or simultaneously. However, when treating individual wrinkles and/or fine lines using such an area treatment arrangement, much of the skin tissue around the wrinkle and/or fine line, which may not necessarily require treatment, is also treated, while the density of the lesions at or immediately around the wrinkle typically is too low. For that reason a different, often higher density, line treatment is preferred. To enable a user to apply the treatment mainly across a wrinkle, the treatment device according to the invention may, for example, emit the laser light via a single one of the predefined locations in the emission window at a pulse rate that, for example, relates to the sensed speed of motion relative to the skin surface to generate the required lesion density along the line of the wrinkle In the embodiment of the treatment device according to the invention, a treatment device having a plurality of predefined locations for emitting laser light from an elongated area is suitable to be used in a line treatment process. Also here the key is to adapt the control signal to generate the required treatment while ensuring that the density of the lesions corresponds to the required density. The treatment device according to the invention switches from the area treatment process to the line treatment process when the speed component of the sensed motion perpendicular to the treatment axis is below the change threshold value. The control signal may, for example, represent different non-zero sequences of the predefined locations for the line treatment process compared to the area treatment process. Therefore, in the line treatment process, the number of lesions outside the treated line may be reduced or even be zero, while too high a density of lesions on the treated line is prevented. The line treatment process may provide a certain reduced width of the area where lesions are applied inside the skin tissue at the treatment location, while in a specific embodiment, in the line treatment process, the treatment device may only apply lesions at a treatment line, not outside the treatment line. Of course, the change from area treatment process to line treatment process may also include other changes in the control signal, such as changes in laser power.

In an embodiment of the treatment device, the area disposition comprises a random disposition of lesions having a predefined lesion density. Such a random disposition of lesions may result in a pseudo random predefined distribution, wherein equally spaced lesions are distributed over an area of the skin, which results in a substantially even coverage of a part of the skin surface and thereby a substantially even outcome of the treatment applied by the treatment device.

In an embodiment of the treatment device, the non-zero sequence is adaptable in dependence on the speed of motion. This adaptability may be used to fine-tune the treatment to a specific skin type that needs to be treated and to allow different levels and severities of treatment. Differences may include, for example, different densities of lesions and different treatment depths, diameters and shapes of the lesions. The lesions may, for example, be circular, cylindrical or elongated. Also different parts of the body may require different types of treatment. Typically, the predefined dispositions may be adapted manually by a user or operator of the treatment device according to the invention. Alternatively, the treatment device may comprise sensors to sense the type of skin that requires treatment and, as a result, may apply the required treatment automatically. Even further alternatively, the treatment device may comprise a sensor for sensing an efficiency of the treatment and adapt the treatment if the sensed efficiency does not correspond to the required efficiency.

In an embodiment of the treatment device, the controller is configured for periodically checking the control signal with a predefined time delay between two subsequent checking events. This predefined time delay may be determined by the processing speed of the controller, the refresh rate of the motion sensor or by the required energy dissipation which might be relatively low due to battery operation of the treatment device. Alternatively, the predefined time delay may depend on, for example, mechanical characteristics of the treatment device, such as the time required to sequentially select each of the predefined locations in the elongated area.

In an embodiment of the treatment device, the predefined time delay depends on the sensed speed of motion of the treatment device across the skin surface. This periodical checking of the control signal is used to enable a motion of the treatment device parallel to the treatment axis, while avoiding too high a density of lesions inside the skin tissue or even overlap of lesions inside the skin tissue. Especially changes in the sensed speed typically require a change of the control signal to continue to maintain this safety measure. Therefore, at higher speeds of the treatment device relative to the skin surface, the checking events should be done more often, so that the predefined time delay becomes shorter. The predefined time delay may also depend on a first derivative of the sensed speed of the treatment device across the skin surface. The larger the speed change sensed, the more important the adaptation of the control signal becomes, and hence the predefined time delay should be short.

In an embodiment of the treatment device, the controller is configured for adapting the control signal if a difference between a previously sensed speed of motion of the treatment device and an actually sensed speed of motion of the treatment device relative to the skin surface is above a speed-change threshold. If the speed change between two subsequent checking events is too small, the controller does not need to change the control signal and the treatment device may continue to operate as previously. The change in control signal may, for example, be a step-wise change in parameters of the control signal and so the speed-change threshold may be a minimum speed change for a single step in this step-wise change of the parameters of the control signal. In addition, this speed-change threshold may result in a power reduction of the treatment device, because the change of the control signal is only done when necessary, saving some processing power of the controller and subsequently saving power of the treatment device. This may be especially beneficial when the treatment device uses batteries as power supply.

In an embodiment of the treatment device, the treatment device further comprises a storage device connected to the controller, the storage device comprising data linking the non-zero sequence to the sensed motion for generating the control signal in dependence on the sensed motion. Any storage device may be used and the data for linking the non-zero sequence to the sensed motion may be stored in the form of a Look-Up Table (further also indicted as LUT). The storage device may comprise a plurality of LUTs, for example, for the different modes of operation of the treatment device. In addition, the storage device may comprise a first LUT comprising the link between the sensed motion perpendicular to the treatment axis and the required non-zero sequence, and a second LUT may comprise correction values with respect to this non-zero sequence from the first LUT to compensate for the motion in a direction parallel to the treatment axis. A benefit when using LUTs is that the change of information may take place relatively fast without requiring too much processing power of the controller. As an alternative, also change algorithms may be included in the storage device, which may be used to calculate the required non-zero sequence when a specific motion of the treatment device relative to the skin surface is sensed.

In an embodiment of the treatment device, the treatment generator comprises a deflection wheel having deflection elements, each deflection element being configured for deflecting the laser light towards one of the plurality of predefined locations. Such a deflection wheel may, for example, be a refraction wheel having refraction elements which are configured for refracting the laser light towards one of the plurality of predefined locations in the emission window. Alternatively, the deflection wheel may, for example, be a reflection wheel, having reflection elements which are configured for reflecting the laser light towards one of the plurality of predefined locations in the emission window.

In an embodiment of the treatment device, the treatment generator comprises an array of treatment lasers, each treatment laser being configured for emitting the laser light towards one of the plurality of predefined locations in the emission window. The plurality of treatment lasers may be arranged at or near the emission window of the treatment device, which may significantly reduce the optical complexity of the treatment device.

In an embodiment of the treatment device, the treatment generator comprises a movable mirror arrangement configured for reflecting the laser light towards individual ones of the plurality of predefined locations in the emission window.

In an embodiment of the treatment device comprising the deflection wheel, the deflection wheel is an axicon deflection wheel. An axicon deflection wheel is shaped such that the laser spot is maintained substantially at the same location on the skin surface while moving the treatment device relative to the skin surface in a certain direction typically in the direction perpendicular to the treatment axis. As a result, the lesions generated using a treatment device having such an axicon deflection wheel substantially resemble needle points. For that reason, the axicon deflection element has a certain shape, ensuring such fixing of the laser spot on the skin surface while moving the treatment device. In a treatment device having an axicon deflection wheel, the speed of the wheel is linked to the sensed motion of the treatment device to ensure this fixing of the position of the laser spot during the treatment. When a motion of the treatment device is sensed in a direction parallel to the treatment axis, this fixing of the position of the laser spot while moving the treatment device may not work, as the axicon deflection wheel may be optimized for one direction of motion only. As a result, the lesions will be elongated in the direction of movement in which the axicon deflection wheel is not optimized. To still ensure that sufficient laser energy is deposited inside the skin tissue to generate lesions, the laser power may need to be adapted when motion parallel to the treatment axis is sensed. Also the density of the lesions may need to be slightly adapted, because now the lesions are elongated and thus cover more of the skin surface than when there is only a movement in the direction perpendicular to the treatment axis.

In an embodiment of the treatment device, the treatment device is a handheld treatment device. Such a handheld treatment device may be operated using batteries or may be connected to mains power via a power cord.

These and other aspects of the invention are apparent from and will be elucidated with reference to the embodiments described hereinafter.

BRIEF DESCRIPTION OF THE DRAWINGS

In the drawings:

FIG. 5A shows a Look-Up Table indicating a relation between the sensed motion and the different control signals, and FIG. 5B shows the lesion locations with respect to the treatment axis for different laser duty cycles when using a deflection wheel.

DETAILED DESCRIPTION OF THE INVENTION

Figure 1:
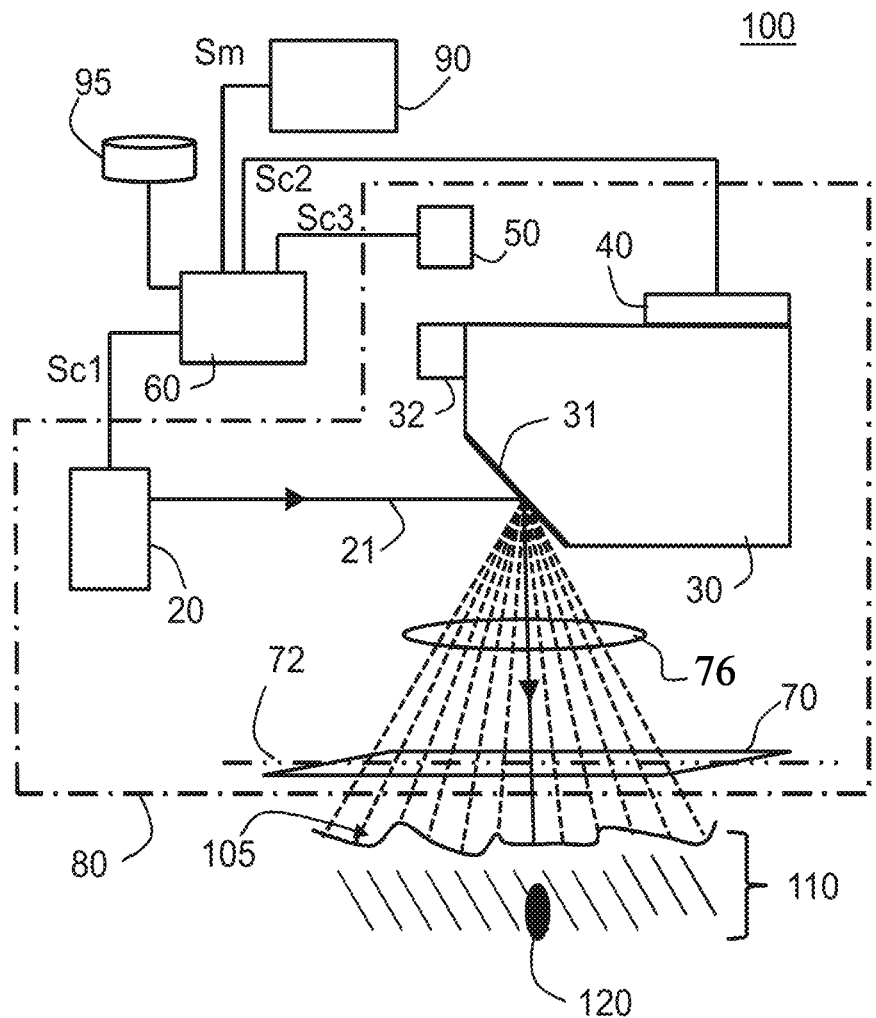
FIG. 1 schematically shows a treatment device according to the invention.

FIG. 1 schematically shows a treatment device 100 according to the invention. The treatment device 100 comprises a treatment laser 20 for providing a light beam 21 and a deflection wheel 30 with a plurality of deflection elements 31 which deflect the light beam 21 through an objective lens 76 and an emission window 70 of the treatment device 100 towards a skin tissue 110. Each deflection element 31 provides a respective different direction of reflection for the light beam 21, causing the reflected light beam 21 to be emitted from the treatment device 100 via different predefined locations 74 in the emission window 70 (see FIG. 4). Accordingly, during rotation of the deflection wheel 30, the treatment device 100 generates a non-zero sequence of at least one of the plurality of predefined locations 74 in the emission window 70 from which the light beam 21 is consecutively reflected towards a corresponding plurality of different positions at the skin surface 105. At the skin surface 105, the light beams enter the skin tissue 110 and create lesions 120 inside the skin tissue 110. Lesions 120 are also known as microscopic treatment zones (MTZs) of thermally denatured skin tissue 110 and the fractional application of lesions 120 creates a predefined disposition of lesions 120 inside the skin tissue 110 which are surrounded by unaffected skin tissue 110. The lesion 120 shown in FIG. 1 is drawn so as to be completely inside the skin tissue 110, but such a lesion 120 may also start already at the skin surface and extend into the skin tissue 110 (not shown). This treatment activates the skin repair mechanisms and, for example, improves skin appearance. The treatment laser 20 is coupled to a control circuit 60 which controls the treatment laser 20 to illuminate individual deflection elements 31 at selected moments. The deflection wheel 30 is rotated by driving means 40, such that the different deflection elements 31 of the deflection wheel 30 successively cross the path of the incoming light beam 21. In the embodiment shown in FIG. 1, the deflection elements 31 constitute reflective facets 31 of which the reflective surfaces are oriented at different angles with respect to the incoming light beam 21 in order to reflect the light beam 21 towards different predefined locations 74 in the emission window 70 to impinge on the skin surface 105 at different locations. Alternatively, the deflection wheel 30 may comprise a refractive element (not shown) for refracting (not shown) the incoming light beam 21 towards the different predefined locations 74 of the emission window 70. Still further alternatively, the deflection wheel 30 may comprise an axicon deflection wheel (not shown), in which the reflective or refractive surface is shaped such that the spot created by the light beam 21 on the skin surface 105 remains substantially static while the treatment device 100 is being moved relative to the skin surface 105. Such axicon deflection wheels are known in the art and the rotation speed of these axicon deflection wheels has to relate to the motion of the treatment device 100 relative to the skin surface 105 to ensure that the spot remains substantially static.

The deflection wheel 30 as shown in FIG. 1 (and also FIGS. 2A and 2B) further comprises triggering flakes 32 which are provided next to the deflection elements 31. A passing motion of the triggering flakes 32 is detected by a flake detector 50. The flake detector 50 is coupled to the control circuit 60. The frequency of the trigger signal generated by the flake detector 50 determines the rotational speed signal Sc2 of the deflection wheel 30. In addition, the control circuit 60 controls a modulation of the light beam 21 based on the trigger signal to select through which of the plurality of predefined locations 74 (see FIG. 4) the treatment light is emitted during the treatment.

The deflection wheel 30 may, for example, comprise twelve deflection elements 31, and the control circuit 60 may, for example, modulate the light beam 21 to provide a light pulse at 2, 4, 6 or even 12 of the deflection elements 31 passing during one rotation. This modulation of the light beam 21 may be used to determine a density of the disposition of lesions 120 inside the skin tissue 110 during the treatment. Furthermore, the device 100 comprises a motion sensor 90 for determining motion of the treatment device 100 relative to the skin surface 105, which is further also indicated as "hand speed" being the speed with which a user drags the treatment device 100 along the skin surface 105. The control circuit 60 is configured to adapt the modulation of the light beam 21 (for example, via controlling an on/off switching of the light source 20) depending on the measured motion (or hand speed) in order to generate the non-zero sequence of the plurality of predefined locations 74 in the emission window 70 from which the laser light 21 is consecutively emitted in dependence on the motion signal to provide the predefined disposition of lesions 120 (or MTZs) at a more or less constant density, being substantially independent of the motion (or hand speed).

In addition to the controlling of the modulation of the light beam 21, the controller 60 is further configured to select the actual deflection element 31 via which the light beam 21 is deflected towards the skin surface 105, and hence to control the actual predefined location 74 via which the light is emitted from the treatment device 100 into the skin tissue 110. The flake detector 50 of treatment device 100 may, for example, receive a specific reply signal from a predefined flake 32 of the plurality of flakes 32, which enables the controller 60 to identify the position of that predefined flake 32, and hence identify a position of a predefined one of the deflection elements 31 and a predefined one of the predefined locations 74 in the emission window 70. When the position of the remainder of the deflection elements 31 is known to the controller 60, the controller 60 may, for example, use the modulation of the light beam 21 to define which of the deflection elements 31 is to be selected to emit the next light beam 21 towards the skin surface 105 to generate the lesion 120 inside the skin tissue 110. The controller 60 may also control a power Sc1 of the treatment laser 20 and, for example, a focusing depth of the treatment laser 20 to enable the severity of the laser based fractional treatment to be varied.

The treatment device 100 according to the invention further comprises a storage device 95 for storing information related to the required modulation of the light beam 21, the required rotational speed of the deflection wheel 30 and other parameters relevant to generate the sequence of predefined locations of the lesions 120 inside the skin tissue 110. Such information may, for example, be stored on the storage device 95 in Look-Up Tables (see FIGS. 5A, 6A and 7A) from which the controller 60 can retrieve the required information, depending on, for example, the sensed motion Sm. The motion sensor 90 may be able to sense a speed of the sensed motion Sm and a direction of the sensed motion Sm. Using these Look-Up Tables, the controller 60 may find specific modulation requirements of the light beam 21 and specific timing requirements to ensure that the correct deflection elements 31 are used to generate the predefined disposition of lesions 120 inside the skin tissue 110.

Figure 2A:
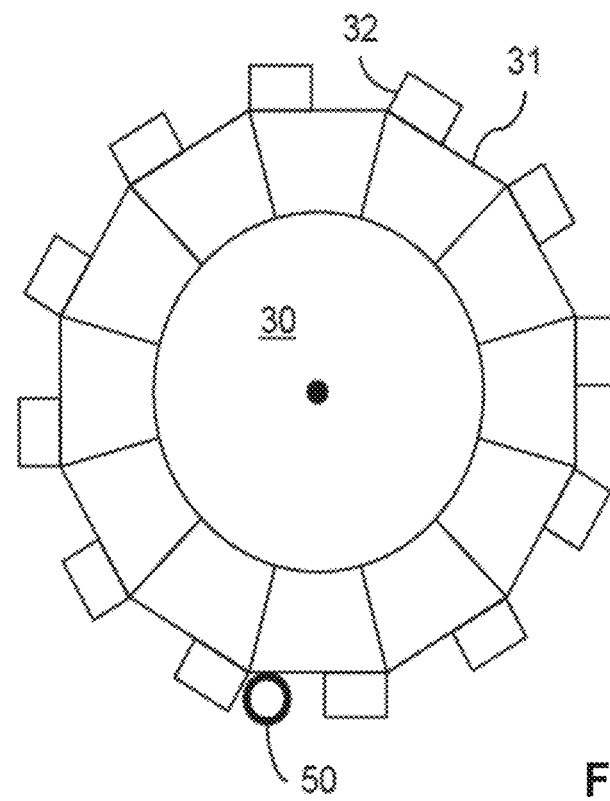
FIGS. 2A and 2B schematically show different views of a deflection wheel of the treatment generator, FIGS. 3A and 3B schematically show different configurations of the treatment generator, FIG. 4 schematically shows an arrangement of predefined locations in the emission window of the treatment device.
Figure 2B:
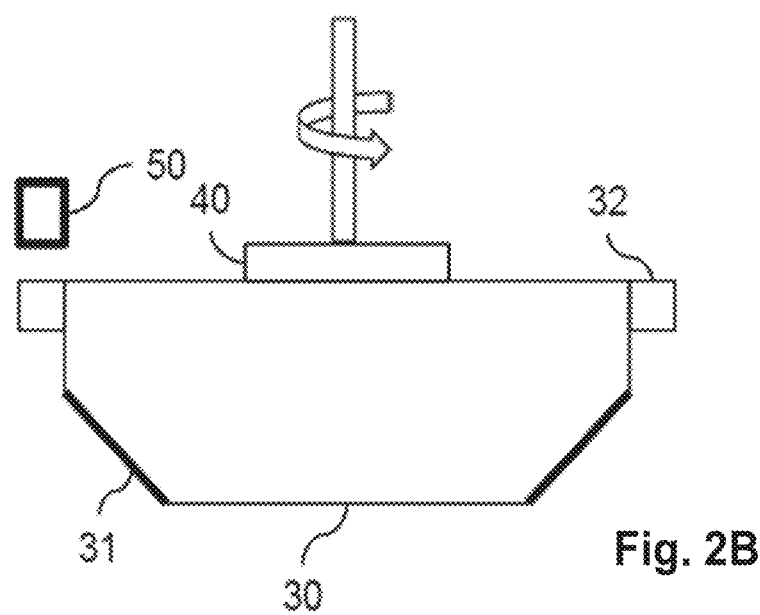

FIGS. 2A and 2B schematically show different views of a deflection wheel 30 of the treatment generator 80, in which the deflection wheel 30 is a reflection wheel 30. FIG. 2A shows a possible location of the flakes 32 relative to the flake detector 50 and FIG. 2B shows a possible embodiment of the deflection elements 31 constituting reflection facets 31. It will be apparent to the person skilled in the art that many variations to such a deflection wheel 30 may be possible. The reflection facets 31 shown in FIGS. 2A and 2B are substantially flat, while in an alternative embodiment the reflection wheel 30 may be an axicon deflection wheel (not shown) in which the deflection elements are curved such that the light beam 21 reflected from these deflection elements remains substantially at the same location on the skin surface 105 during the deflection from that deflection element. A benefit of such an arrangement is that the lesions 120 are not elongated due to the moving of the treatment device 100 and therefore less light energy is required to efficiently generate lesions 120 inside the skin tissue.

Figure 3A:
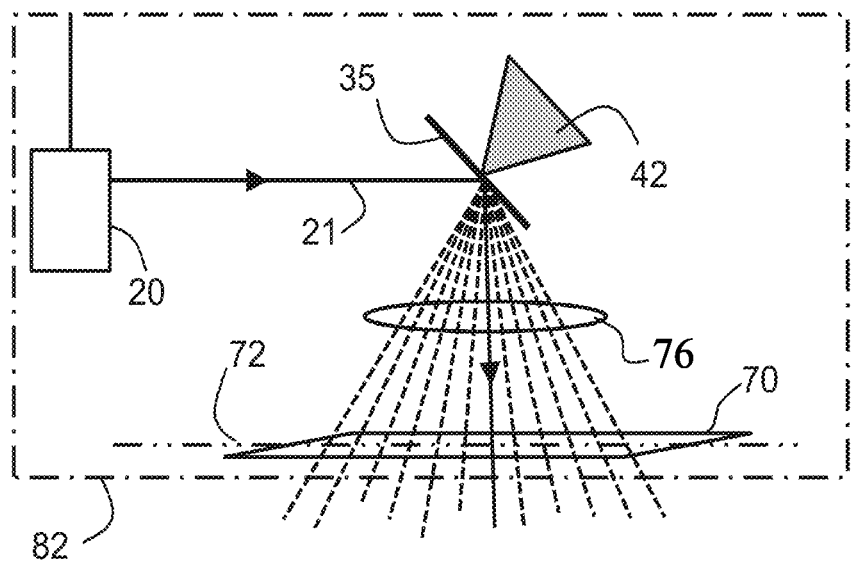
Figure 3B:
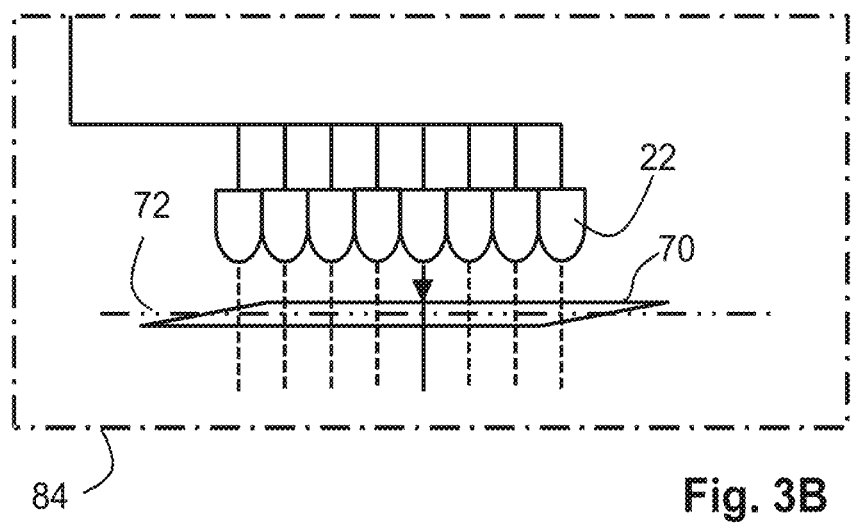

FIGS. 3A and 3B schematically show different configurations of the treatment generator 82, 84 for a treatment device 100 according to the invention. In FIG. 3A, the treatment generator 82 comprises a movable mirror arrangement 35 configured for moving the light beam 21 towards individual ones of the plurality of predefined locations 74 (see FIG. 4) in the elongated area (see FIG. 4) of the emission window 70. The treatment generator 82 further comprises a mirror actuator 42 which is controlled by the controller 60 for controlling a position of the movable mirror arrangement 35 to reflect the light beam 21 to the required location in the emission window 70. Also shown in FIG. 3A are the treatment laser 20, treatment axis 72 and objective lens 76, similar to the elements shown in the treatment generator of FIG. 1.

FIG. 3B shows an array of treatment lasers 22 arranged such that the light from the individual treatment lasers 22 of the array of treatment lasers 22 is emitted via individual ones of the plurality of predefined locations 74 in the emission window 70. A benefit of this arrangement is that there are no moving elements such as a deflection wheel 30 or a movable mirror arrangement 35. Each of the treatment lasers 22 may be controlled by the controller 60 to generate the required disposition of lesions inside the skin tissue 110.

Figure 4:
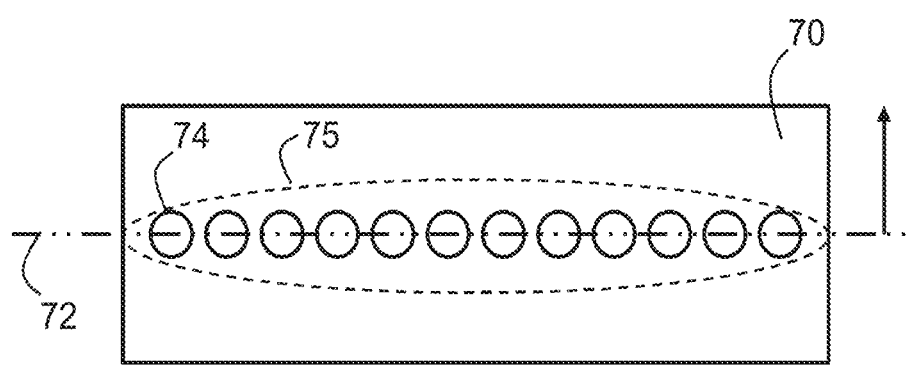

FIG. 4 schematically shows an arrangement of predefined locations 74 in the emission window 70 of the treatment device 100. Each of these arrangements of predefined locations 74 may be produced by any of the treatment generators 80, 82, 84 shown in FIGS. 1, 3A and 3B. For example, FIG. 4A shows an arrangement of predefined locations 74 which are disposed in a single row on the treatment axis 72 within the elongated area 75. In another embodiment, the arrangement of predefined locations 74 may be disposed on either side of the treatment axis 72 within the elongated area 75 in the emission window 70. Generally, the invention covers any embodiment wherein the predefined locations 74 are arranged in an array which extends along the treatment axis 72 of the window 70. Generally the elongated array has an elongated direction of extension which coincides with the direction of the treatment axis 72. More specifically, the elongated array has a central axis of extension in the elongated direction, which central axis of extension coincides with the treatment axis 72. More specifically, each predefined location 74 in the array is located at a distance from the treatment axis 72, seen in a direction perpendicular to the treatment axis 72, which is smaller than 25% of a maximum distance between two predefined locations in the array, seen in a direction parallel to the treatment axis 72. In the embodiment of FIG. 4, the distance between each predefined location 74 and the treatment axis 72 is zero. In another embodiment, said maximum distance between two predefined locations in the array is the distance between the predefined locations 74 most left and most right in the figure, seen in a direction parallel to the treatment axis 72, and each predefined location 74 is at a distance from the treatment axis equal to about 5% of said maximum distance.

FIG. 5A shows a Look-Up Table indicating a relation between the sensed motion (indicated as hand speed) and the different control signals to achieve a specific disposition of lesions 120 inside the skin tissue 110. The "fire frequency" is directly related to the number of lesions 120 which are created per square centimeter. The laser duty cycle relates to the number of lesions 120 (or to the fire frequency) times a laser pulse width. The laser pulse width is related to the rotational speed of the deflection wheel 30. The full energy of a pulse may be deposited in a single lesion and therefore via a single facet of the deflection wheel 30.

In view of these variables there are numerous ways based on all the variables to configure the fire frequency and duty cycle to obtain the required area coverage in relation to the sensed hand speed Vh and the rotational speed of the deflection wheel 30. The laser duty cycle provides an indication of the percentage of time the laser 20 is on. As an example, when the laser 20 fires 30 pulses per second, wherein every pulse is 10 milliseconds in duration, the total time the laser 20 is on is 30×0.01=0.3 times 100%, resulting in a 30% duty cycle. If, however, less deep lesions 120 are required, the laser pulse may be reduced to 5 milliseconds, resulting in a laser duty cycle of 15%.

The energy per pulse to create a lesion 120 is equal to the time during which the laser 20 is switched on times the power of the laser 20 (for example, the power of a laser diode). As an example, if a laser of 1 Watt was used and the pulse duration was 10 milliseconds, the energy to create a lesion would be 1×0.01=10 milliJoule. As can be seen from the Look-Up Table of FIG. 5A, the controller 60 can find the light beam modulation and treatment laser duty cycle, and FIG. 5B shows the lesion locations with respect to the treatment axis 72 for different laser duty cycles to ensure that the number of lesions 120 per square centimeter (indicated in the Look-Up Table of FIG. 5A as "Area Coverage") remains substantially constant in this case being 30 lesions per square centimeter. In this example there are 8 deflection elements 31, the pulse duration is 2.78 milliseconds, and a single rotation of the deflection wheel 30 takes 44.48 milliseconds (rotation frequency is 22 times per second). However, the deflection wheel 30 may also have more deflection elements 31 as shown in FIG. 2A and the rotational speed of the deflection wheel 30 may be adapted. The exact location of the deflection elements 31 may not always be needed, only when a specific pattern should be created. The table shown in FIG. 5B shows the location of the deflection elements 31 depending on the laser duty cycle.

Returning briefly to FIG. 4, the arrangement of predefined locations 74 shown in FIG. 4 is chosen such that, when moving the treatment device 100 relative to the skin surface 105 in a direction substantially perpendicular to the treatment axis 72 (indicated with the arrow), none of the lesions 120 overlap. Because overlap of lesions 120 during the treatment should be avoided, the known treatment device is only allowed to be moved substantially perpendicularly to the treatment axis 72 during the treatment. When the motion sensor 90 in the known treatment devices detects that a component of the sensed motion parallel to the treatment axis 72 is above a predefined threshold, the known treatment device switches off as a control measure to prevent that two lesions 120 are generated too close together during scanning or to prevent that two lesions 120 overlap, because each of these events may generate too much damage inside the skin tissue 110. This switching off of the known treatment device significantly reduces the freedom of operation of the known treatment device.

Figures 6A, 6B:
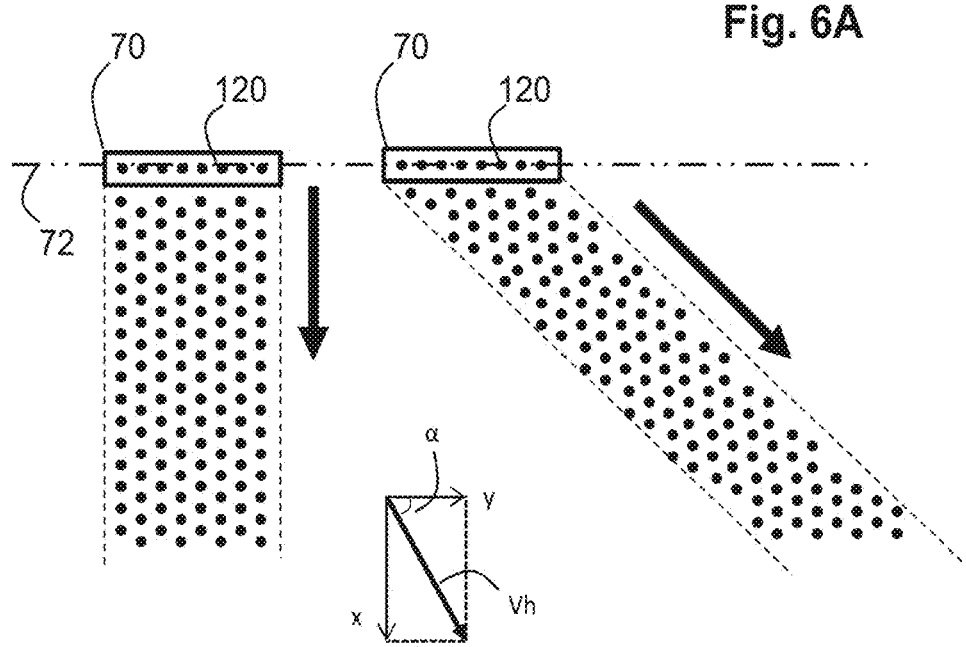
FIG. 6A shows a Look-Up Table according to the invention, listing control signals for different sensed speeds parallel to the treatment axis.
FIG. 6B shows a lesion distribution when the motion is perpendicular to the treatment axis and when the motion is at an angle a to the treatment axis.

FIG. 6A shows a Look-Up Table for a treatment device 100 according to the invention. This Look-Up Table lists control signals in the case of a first component of the sensed motion Sm parallel to the treatment axis 72 being above a first threshold. The sensed motion (or hand speed) is a vector Vh and may, for example, be divided into a first component parallel to the treatment axis 72 (in the table of FIG. 6A and in FIG. 6B this is in the y-direction) and into a second component perpendicular to the treatment axis 72 (in the table of FIG. 6A and in FIG. 6B this is in the x-direction).

The Look-Up Table shown in FIG. 6A has been adapted such that the "area coverage" of the treatment device 100 remains the same as shown in FIGS. 5A and 5B (being 30 lesions per square centimeter), while now allowing a substantial movement component in the direction parallel to the treatment axis 72 (while maintaining the remainder of the parameters of FIGS. 5A and 5B substantially the same, such as 8 deflection elements 31, a pulse duration of 2.78 milliseconds, and a single rotation of the deflection wheel 30 taking 44.48 milliseconds corresponding to a rotation frequency of 22 Hz). This adapted Look-Up Table significantly increases the freedom to operate the treatment device as compared to the known treatment device, as it allows less strict movement of the treatment device 100 according to the invention compared to the known treatment device, while still avoiding lesions 120 to be generated too close together or even to overlap. FIG. 6B shows an example of such a resulting lesion 120 distribution.

As an alternative to the Look-Up Table shown in FIG. 6A, the controller 60 may comprise a formula for calculating a correction value to correct the Look-Up Table as shown in FIG. 5A to correct for movement with a component parallel to the treatment axis 72. Such a correction value may be used to correct the control signals Sc1, Sc2, Sc3 (see FIG. 1) from the Look-Up Table of FIG. 5A. An example of such formula may be:

$$\text{Laser duty cycle} = \text{pulse duration laser} \cdot \cos(90-\alpha) \cdot \text{hand speed} \cdot \text{lesions/cm}^2 \cdot 100\%$$

Figures 7A, 7B:
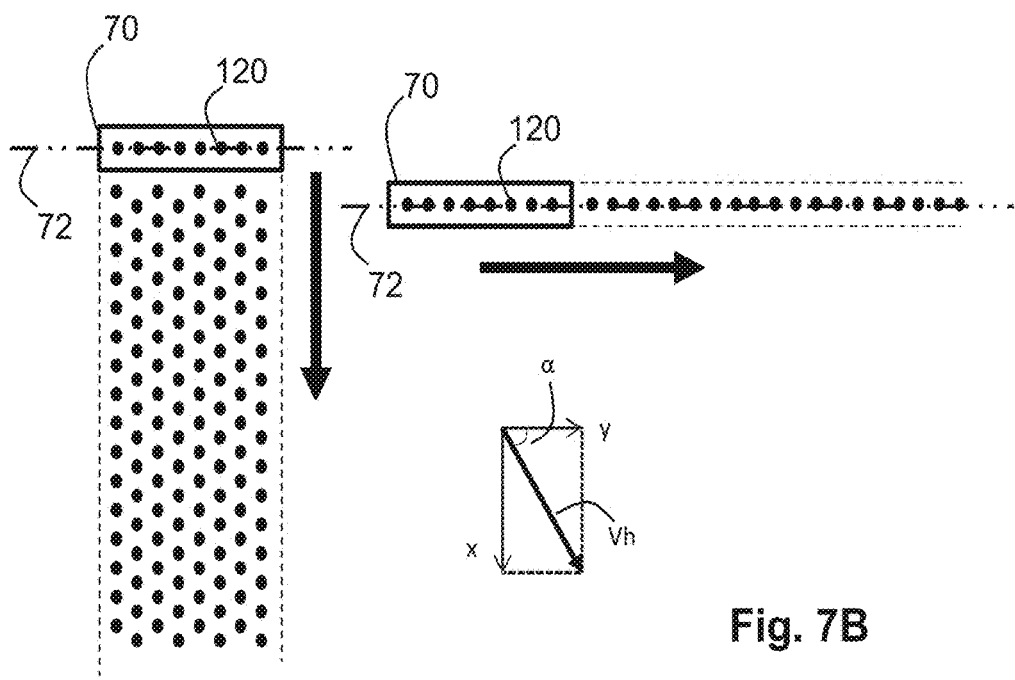
FIG. 7A shows a Look-Up Table according to the invention, listing control signals when the motion is only substantially parallel to the treatment axis.
FIG. 7B shows a lesion distribution when the motion is perpendicular to the treatment axis and parallel to the treatment axis.

FIG. 7A shows a Look-Up Table according to the invention, listing control signals for the treatment device 100 according to the invention when the sensed motion of the treatment device relative to the skin surface only has a component in a direction parallel to the treatment axis 72. In this case, the controller 60 determines a non-zero sequence of at least one of the plurality of predefined locations 74 in the emission window 70 from which the laser light is consecutively emitted in dependence on the motion signal Vh. Thus, in accordance with the invention, the controller 60 is configured to activate the treatment generator 80 to generate the non-zero sequence when the sensed motion of the treatment device 100 relative to the skin surface only has a component in the direction parallel to the treatment axis. This is a special case of the Look-Up Table as shown in FIG. 6A in which the angle α=0 degrees. In the embodiments shown in FIGS. 5A, 5B, 6A and 6B, the treatment process applied is an area treatment process in which in a single movement of the treatment device 100 an area as broad as the elongated area 75 may be treated. Such an area treatment process is often used for the treatment of unevenness of the skin tissue 110, or pigmentation or dischromia issues of the skin tissue 110. For such an area treatment to be time-effective, the treatment device 100 comprises a row or array of predefined locations 74 (see for example, FIG. 4) from which laser light 21 may be emitted from the emission window 70 to treat multiple positions sequentially or simultaneously. However, when treating individual wrinkles or fine lines, using such an area treatment process, much of the skin tissue 110 around the wrinkle or fine line, which may not necessarily require treatment, is also treated. Furthermore, the density of the lesions 120 at or immediately around the wrinkle or fine line typically is too low when using an area treatment process. For that reason a different, often higher density, line treatment is preferred. A treatment device for such a line treatment typically emits the laser light via a single location at a pulse rate that relates to the sensed motion speed relative to the skin surface to generate the required lesion density. However, in the treatment device 100 according to the invention, the plurality of predefined locations 74 for emitting laser light 21 from the emission window is provided. To provide a line treatment process, the treatment device 100 according to the invention generates the non-zero sequence when the sensed motion of the treatment device 100 relative to the skin surface only has a component in the direction parallel to the treatment axis 72. To provide a line treatment process, the treatment device 100 according to the invention may, for example, adapt the control signals Sc1, Sc2, Sc3 to generate the required treatment while ensuring that the density of the lesions 120 still corresponds to the required density, and/or to avoid overlap of lesions 120 during treatment. In particular, the treatment device 100 according to the invention switches from the area treatment process to the line treatment process when a component of the sensed motion perpendicular to the treatment axis 72 is below a change threshold value (in the current embodiment, the Look-Up Table in FIG. 7A shows no movement in the x-direction). As a result, the controller 60 retrieves the control signals Sc1, Sc2, Sc3 from a different Look-Up Table such as the one shown in FIG. 7A to generate the lesion distribution as shown in FIG. 7B which provides the line treatment process. For example, the non-zero sequence of the treatment locations 74 for the line treatment process may be different compared to the area treatment process. Therefore, the line treatment process may limit the amount of lesions outside the treated line while still preventing overlap of lesions 120 and/or preventing too high a density of lesions 120 along the line. Of course, the change from the area treatment process to the line treatment process may also include other changes in the control signals Sc1, Sc2, Sc3, such as changes in laser power. And, also similarly, instead of using a new Look-Up Table as shown in FIG. 7A, the treatment device 100 may comprise a further formula for calculating a correction value to correct, for example, the Look-Up Table as shown in FIG. 5A for movements parallel to the treatment axis 72. Such a correction value may be used to correct the control signals Sc1, Sc2, Sc3 (see FIG. 1) from the Look-Up Table of FIG. 5A.

In summary, the invention provides a treatment device 100 for fractional laser-based skin treatment. The treatment device comprises an emission window comprising an elongated area and a plurality of predefined locations in said elongated area, wherein the predefined locations are arranged in an elongated array which extends along a treatment axis of the window, and wherein each predefined location in the array is located at a distance from the treatment axis, seen in a direction perpendicular to the treatment axis, which is smaller than 25% of a maximum distance between two predefined locations in the array, seen in a direction parallel to the treatment axis. The treatment device further comprises a treatment generator 80 comprising a treatment laser 20 for emitting laser light 21 towards skin tissue 110 from said plurality of predefined locations 74 in the emission window 70 for generating, in use, laser-based lesions 120 inside the skin tissue 110. The treatment device further comprises a motion sensor 90 for sensing motion of the treatment device relative to the skin surface 105 and a controller 60 for determining a non-zero sequence of at least one of the plurality of predefined locations in the emission window from which laser light is consecutively emitted in dependence on the motion signal. The controller is configured to activate the treatment generator to generate said non-zero sequence when the sensed motion of the treatment device relative to the skin surface only has a component in a direction parallel to the treatment axis.

It will be appreciated that the invention especially many of the method steps indicated above—also extends to computer programs, particularly computer programs on or in a carrier, adapted for putting the invention into practice. The program may be in the form of source code, object code, a code intermediate source code and object code such as a partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or system capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such electrical or optical cable or other system or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the system claim enumerating several means, several of these means may be embodied by one and the same item of hardware. The mere fact that certain measures are recited in mutually different dependent claims does not indicate that a combination of these measures cannot be used to advantage.

The invention claimed is:

1. A treatment device for fractional laser-based skin treatment, the treatment device comprising:
   an emission window comprising an elongated area;
   a treatment generator comprising a treatment laser, the treatment generator being configured to emit laser light towards skin tissue from a plurality of predefined locations in the emission window for generating, in use, laser-based lesions inside the skin tissue, wherein said plurality of predefined locations are disposed on a treatment axis of the emission window in said elongated area of the emission window;
   a motion sensor configured to sense motion of the treatment device relative to the skin surface and to generate a motion signal representative of the sensed motion; and
   a controller configured to receive the motion signal for determining a non-zero sequence of at least one of the plurality of predefined locations in the emission window from which the laser light is consecutively emitted in dependence on the motion signal, and for activating the treatment generator to generate said non-zero sequence based on a control signal representative of said non-zero sequence,
   wherein the controller is configured to activate the treatment generator to generate said non-zero sequence when the sensed motion of the treatment device relative to the skin surface only has a component in a direction parallel to the treatment axis.

2. The treatment device according to claim 1, wherein the controller is configured to activate the treatment generator to generate said non-zero sequence when, independent of a direction of the sensed motion relative to the treatment axis, a speed of the sensed motion is above a treatment threshold value.

3. The treatment device according to claim 1, wherein the controller is configured to control a power of the treatment laser in dependence on the motion signal.

4. The treatment device according to claim 1, wherein the sensed motion comprises speed and direction of the treatment device with respect to the treatment axis relative to the skin surface.

5. The treatment device according to claim 1, the treatment device being configured to apply an area treatment process wherein, upon motion of the treatment device in a direction perpendicular to the treatment axis, wherein the treatment device generates an area disposition of lesions inside the skin tissue having a width equal to a length of the elongated area of the emission window.

6. The treatment device according to claim 5, wherein the area disposition comprises a random disposition of lesions having a predefined lesion density.

7. The treatment device according to claim 5, the treatment device being configured to apply a line treatment process, wherein the treatment device generates a line disposition of lesions inside the skin tissue different from the area disposition, the controller being configured to change from the area treatment process to the line treatment process when a speed component of the sensed motion perpendicular to the treatment axis is below a change threshold value.

8. The treatment device according to claim 1, wherein controller is configured to adapt the non-zero sequence in dependence on a speed of the sensed motion sensed by the motion sensor.

9. The treatment device according to claim 1, wherein the controller is configured for periodically checking the control signal with a predefined time delay between two subsequent checking events.

10. The treatment device according to claim 9, wherein the predefined time delay depends on a speed of the sensed motion of the treatment device across the skin surface.

11. The treatment device according to claim 9, wherein the controller is configured to adapt the control signal when a difference between a previously sensed speed of motion of the treatment device and an actually sensed speed of motion of the treatment device relative to the skin surface is above a speed-change threshold.

12. The treatment device according to claim 1, wherein the treatment device further comprises a storage device connected to the controller, the storage device comprising data linking the non-zero sequence to the sensed motion for generating the control signal in dependence on the sensed motion.

13. The treatment device according to claim 1, wherein the treatment generator
comprises a deflection wheel having deflection elements, each deflection element being configured for deflecting the laser light towards one of the plurality of predefined locations.

14. The treatment device according to claim 1, wherein the treatment device is a handheld treatment device.

15. The treatment device according to claim 1, wherein the treatment generator comprises an array of treatment lasers, each treatment laser being configured for emitting the laser light towards one of the plurality of predefined locations.

16. The treatment device according to claim 1, wherein the treatment generator comprises a movable mirror arrangement configured for reflecting the laser light towards individual ones of the plurality of predefined locations.

* * * * *